(12) United States Patent
Yoshida et al.

(10) Patent No.: US 11,918,322 B2
(45) Date of Patent: Mar. 5, 2024

(54) INTRAORAL SENSING APPARATUS AND MANUFACTURING METHOD THEREOF

(71) Applicants: SEIKO GROUP CORPORATION, Tokyo (JP); SHOWA UNIVERSITY, Tokyo (JP)

(72) Inventors: Yoshifumi Yoshida, Tokyo (JP); Ryosuke Isogai, Tokyo (JP); Kotaro Maki, Tokyo (JP); Rumi Shiotsu, Tokyo (JP)

(73) Assignees: SEIKO GROUP CORPORATION, Tokyo (JP); SHOWA UNIVERSITY, Tokyo (JP)

( * ) Notice: Subject to any disclaimer, the term of this patent is extended or adjusted under 35 U.S.C. 154(b) by 250 days.

(21) Appl. No.: 17/196,069

(22) Filed: Mar. 9, 2021

(65) Prior Publication Data
US 2021/0282651 A1    Sep. 16, 2021

(30) Foreign Application Priority Data

Mar. 13, 2020 (JP) .................. 2020-044440
Dec. 28, 2020 (JP) .................. 2020-219158

(51) Int. Cl.
*A61B 5/0205* (2006.01)
*A61B 5/00* (2006.01)
(Continued)

(52) U.S. Cl.
CPC ........ *A61B 5/02055* (2013.01); *A61B 5/0002* (2013.01); *A61B 5/02108* (2013.01); *A61B 5/02427* (2013.01); *A61B 5/0261* (2013.01); *A61B 5/14552* (2013.01); *A61B 5/682* (2013.01); *A61C 13/20* (2013.01);
(Continued)

(58) Field of Classification Search
CPC . A61B 5/02055; A61B 5/002; A61B 5/02108; A61B 5/02427; A61B 5/0261; A61K 6/889; A61K 6/893; A61K 6/896
See application file for complete search history.

(56) References Cited

U.S. PATENT DOCUMENTS 3,709,866 A * 1/1973 Waller .................... A61K 6/20
                                                        524/871
4,629,424 A * 12/1986 Lauks .................... A61B 5/11
                                                        455/100

(Continued)

FOREIGN PATENT DOCUMENTS

JP    2011-066080 A    3/2011
WO   WO 2017/218947 A1   12/2017

OTHER PUBLICATIONS

Extended European Search Report in Europe Application No. 21161634.7, dated Jul. 23, 2021, 9 pages.

*Primary Examiner* — Nicholas D Lucchesi
(74) *Attorney, Agent, or Firm* — Crowell & Moring LLP

(57) ABSTRACT

The present intraoral sensing apparatus is configured to be installed in an oral cavity, and is provided with an electronic device equipped with electronic components mounted on a circuit board; a first dental resin material which completely covers the electronic device; a second dental resin material which completely covers the first dental resin material; and an intraoral instrument having a first recess in which the electronic device covered with the first dental resin material and the second dental resin material is accommodated.

18 Claims, 10 Drawing Sheets

(51) Int. Cl.
*A61B 5/021* (2006.01)
*A61B 5/024* (2006.01)
*A61B 5/026* (2006.01)
*A61B 5/1455* (2006.01)
*A61C 13/20* (2006.01)
*A61K 6/889* (2020.01)
*A61K 6/893* (2020.01)
*A61K 6/896* (2020.01)

(52) U.S. Cl.
CPC .............. *A61K 6/889* (2020.01); *A61K 6/893* (2020.01); *A61K 6/896* (2020.01); *A61B 2562/0219* (2013.01); *A61B 2562/0247* (2013.01); *A61B 2562/0261* (2013.01); *A61B 2562/0271* (2013.01); *A61B 2562/12* (2013.01)

(56) References Cited

U.S. PATENT DOCUMENTS

| | | | | |
|---|---|---|---|---|
| 5,063,255 A * | 11/1991 | Hasegawa | ................ | A61K 6/90 523/109 |
| 5,691,539 A * | 11/1997 | Pfeiffer | .................. | A61B 6/145 378/191 |
| 6,212,435 B1 * | 4/2001 | Lattner | ................. | A61N 1/0548 607/42 |
| 6,239,705 B1 * | 5/2001 | Glen | ..................... | G08B 21/028 340/573.4 |
| 6,613,001 B1 * | 9/2003 | Dworkin | ................... | A61C 7/00 600/590 |
| 7,328,706 B2 * | 2/2008 | Bardach | ............... | A63B 71/085 128/846 |
| 8,433,083 B2 * | 4/2013 | Abolfathi | ............... | B33Y 80/00 381/322 |
| 10,888,396 B2 * | 1/2021 | Shanjani | .................. | H04Q 9/00 |
| 11,576,766 B2 * | 2/2023 | Shanjani | .................. | A61B 5/682 |
| 2007/0065768 A1 * | 3/2007 | Nadav | ...................... | A61C 7/08 433/18 |
| 2007/0106138 A1 * | 5/2007 | Beiski | .................... | A61B 5/682 600/549 |
| 2009/0210032 A1 * | 8/2009 | Beiski | .................. | A61N 1/0548 264/16 |
| 2010/0152599 A1 * | 6/2010 | DuHamel | ............ | A61B 5/0803 713/153 |
| 2014/0371824 A1 | 12/2014 | Mashiach et al. | | |
| 2015/0173856 A1 * | 6/2015 | Lowe | ....................... | A61C 7/00 433/2 |
| 2017/0252140 A1 | 9/2017 | Murphy et al. | | |
| 2018/0000565 A1 * | 1/2018 | Shanjani | .................. | A61C 7/08 |

* cited by examiner

INTRAORAL SENSING APPARATUS AND MANUFACTURING METHOD THEREOF

RELATED APPLICATIONS

This application claims priority to Japanese Patent Application No. 2020-044440, filed on Mar. 13, 2020, and Japanese Patent Application No. 2020-219158, filed Dec. 28, 2020, the entire content of which is incorporated herein by reference.

BACKGROUND OF THE INVENTION

1. Field of the Invention

The present invention relates to an intraoral sensing apparatus and a manufacturing method thereof.

2. Description of the Related Art

An intraoral sensing apparatus that is installed in the oral cavity to obtain biometric information has been put into practical use.

Conventionally, in a case where an electronic device such as a biometric monitoring sensor is mounted in an intraoral instrument, the electronic device is mounted in the intraoral instrument using a resin having adhesion to both the intraoral instrument and the electronic device. Here, in a case where the electronic device needs to be taken out from the intraoral instrument due to recharging of a battery of the electronic device, or the like, there are problems that the electronic device cannot be taken out because the resin strongly adheres to the electronic device, and when taking out the electronic device forcibly is attempted, the electronic device is damaged. As a means for solving these problems, a method of dissolving the resin for bonding the electronic device to the intraoral instrument using a solvent to take out the electronic device may be conceived. However, since the electronic device is equipped with a battery, a problem that a short-circuit may occur between circuit terminals and damage the electronic device due to immersion in the solvent is also conceivable.

With respect to such a problem, a means for completely covering an electronic device with a material of an intraoral instrument may be employed. For example, Japanese Unexamined Patent Application, First Publication No. 2011-66080 discloses a method for covering a mounting structure with a protective film, which forms a protective film having moisture resistance and insulation properties on at least a part requiring moisture resistance and insulation properties in an electronic circuit board on which an electronic component is mounted, and includes a first process of applying a first coating agent containing a resin to form a first film; and a second process of applying a second coating agent to which an additive imparting a thickening property to the first coating agent has been added, to form a second film. In this case, the electronic device is less likely to be damaged when it is taken out because the electronic device and the intraoral instrument are not bonded to each other. However, when this means is employed, the thickness of the material of the intraoral instrument needs to be increased for manufacture, and in the case of an orthodontic instrument, for example, there is a problem that it is difficult to control a force applied to a row of teeth. Further, if the material of the intraoral instrument cracks, there is also a problem that the electronic device may break because the electronic device directly comes into contact with moisture. For safety, it is necessary to provide a second means such that a short circuit or the like does not occur when one means (in this case, the material of an orthodontic instrument) has cracked. Since only one means is provided in the above-described method, there is also a safety issue. In addition, a dental resin material for fixing the intraoral instrument and the electronic device is obtained by polymerizing and curing a liquid and a liquid, and thus there is a problem that liquid viscosity is low and thus the dental resin material may run off before curing.

With respect to such problems, a construction of an intraoral instrument 41 equipped with an electronic device 42 sandwiched between two sealing films formed of a thermoplastic polymeric compound, as shown in FIG. 17, is conceivable, but it is necessary to further simplify a manufacturing process thereof.

SUMMARY OF THE INVENTION

An object of the present invention is to provide an intraoral sensing apparatus that is easily manufactured and has high safety in use and a manufacturing method thereof.

An intraoral sensing apparatus of the present invention is a sensing apparatus configured to be installed in an oral cavity, and includes: an electronic device equipped with electronic components mounted on a circuit board; a first dental resin material which completely covers the electronic device; a second dental resin material which completely covers the first dental resin material; and an intraoral instrument having a first recess in which the electronic device covered with the first dental resin material and the second dental resin material is accommodated.

In a first specific aspect of the intraoral sensing apparatus of the present invention, the second dental resin material bonds the electronic device covered with the first dental resin material to the inside of the first recess.

In a second specific aspect of the intraoral sensing apparatus of the present invention, a thickness of the second dental resin material at two or more corners of a surface facing a bottom surface which is one of wide surfaces of the first dental resin material is less than a thickness at other portion of the surface; and the first recess is provided with first protrusions at positions corresponding to portions where the thickness of the corners of the second dental resin material is less than the thickness of the other portion.

In a third specific aspect of the intraoral sensing apparatus of the present invention, the second dental resin material is provided with a second recess at two or more surfaces corresponding to side surfaces with respect to a bottom surface which is one of wide surfaces of the first dental resin material; and the first recess is provided with a first protrusion at a position corresponding to the second recess of the side surfaces of the second dental resin material.

In a fourth specific aspect of the intraoral sensing apparatus of the present invention, the second dental resin material is provided with a second protrusion at two or more surfaces corresponding to side surfaces with respect to a bottom surface which is one of wide surfaces of the first dental resin material; and the first recess is provided with a recess at a position corresponding to the second protrusion of the side surfaces of the second dental resin material.

A method of manufacturing the intraoral instrument of the present invention according to a first specific aspect includes: preparing an electronic device equipped with electronic components mounted on a circuit board; completely covering the electronic device with a first dental resin material; preparing a tooth mold matching the teeth and gums of a user at which the intraoral sensing apparatus is to be mounted; placing the electronic device covered with the first dental resin material in the tooth mold; performing press molding by pressing the tooth mold onto an intraoral instrument manufacturing material to mold an intraoral instrument having a first recess in which the electronic device covered with the first dental resin material is to be accommodated; removing the intraoral instrument from the tooth mold in a state in which the electronic device covered with the first dental resin material is accommodated in the first recess; and covering the electronic device covered with the first dental resin material with a second dental resin material such that the second dental resin material completely covers the first dental resin material and is bonded to the inside of the first recess of the intraoral instrument.

A method of manufacturing the intraoral instrument of the present invention according to a second specific aspect includes: preparing an electronic device equipped with electronic components mounted on a circuit board; completely covering the electronic device with a first dental resin material; covering the electronic device covered with the first dental resin material with a second dental resin material such that the second dental resin material completely covers the first dental resin material, and a thickness of the second dental resin material at two or more corners of a surface facing a bottom surface which is one of wide surfaces of the first dental resin material is less than a thickness at other portion of the surface; preparing a tooth mold matching the teeth and gums of a user at which the intraoral sensing apparatus is to be installed; placing the electronic device covered with the first dental resin material and the second dental resin material in the tooth mold; performing press molding by pressing the tooth mold onto a material for manufacturing an intraoral instrument to mold an intraoral instrument having a first recess in which the electronic device covered with the first dental resin material and the second dental resin material is to be accommodated; and removing the intraoral instrument from the tooth mold in a state in which the electronic device covered with the first dental resin material and the second dental resin material is accommodated in the first recess.

A method of manufacturing the intraoral instrument of the present invention according to a third specific aspect includes: preparing an electronic device equipped with electronic components mounted on a circuit board; completely covering the electronic device with a first dental resin material; covering the electronic device covered with the first dental resin material with a second dental resin material such that the second dental resin material completely covers the first dental resin material, and a second recess is provided at two or more surfaces corresponding to side surfaces with respect to a bottom surface which is one of wide surfaces of the first dental resin material; preparing a tooth mold matching the teeth and gums of a user at which the intraoral sensing apparatus is to be installed; placing the electronic device covered with the first dental resin material and the second dental resin material in the tooth mold; performing press molding by pressing the tooth mold onto a material for manufacturing an intraoral instrument to mold an intraoral instrument having a first recess in which the electronic device covered with the first dental resin material and the second dental resin material is to be accommodated; and removing the intraoral instrument from the tooth mold in a state in which the electronic device covered with the first dental resin material and the second dental resin material is accommodated in the first recess.

A method of manufacturing the intraoral instrument of the present invention according to a fourth specific aspect includes: preparing an electronic device equipped with electronic components mounted on a circuit board; completely covering the electronic device with a first dental resin material; covering the electronic device covered with the first dental resin material with a second dental resin material such that the second dental resin material completely covers the first dental resin material, and a second protrusion is provided at two or more surfaces corresponding to side surfaces with respect to a bottom surface which is one of wide surfaces of the first dental resin material; preparing a tooth mold matching the teeth and gums of a user at which the intraoral sensing apparatus is to be installed; placing the electronic device covered with the first dental resin material and the second dental resin material in the tooth mold; performing press molding by pressing the tooth mold onto a material for manufacturing an intraoral instrument to mold an intraoral instrument having a first recess in which the electronic device covered with the first dental resin material and the second dental resin material is to be accommodated; and removing the intraoral instrument from the tooth mold in a state in which the electronic device covered with the first dental resin material and the second dental resin material is accommodated in the first recess.

According to the present invention, it is possible to provide an intraoral sensing apparatus that is easily manufactured and has high safety in use and a manufacturing method thereof.

DETAILED DESCRIPTION OF THE PREFERRED EMBODIMENTS

The present invention has the following advantageous features.

Since an electronic device 2 is doubly covered with a first dental resin material 3 and a second dental resin material 4 when being used in the oral cavity and thus, even if any of the dental resin materials cracks, it is protected by the other one, and thus the electronic device 2 has high safety with respect to a human body. In particular, when the first dental resin material 3 is a silicone resin, the first dental resin material 3 can be easily detached from the electronic device 2 and thus the electronic device 2 can be reused without being damaged because the silicone resin is not bonded to the electronic device 2. Further, a battery mounted in the electronic device 2 can be exchanged by detaching the first dental resin material 3 from the electronic device 2, and thus the present invention is useful particularly when the battery is a primary battery.

Figure 1:
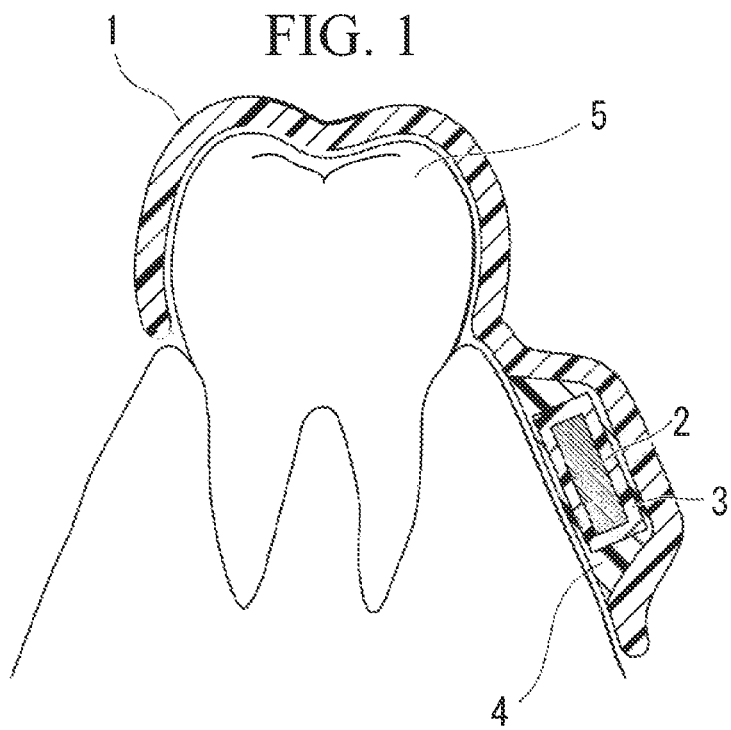
FIG. 1 is a cross-sectional view of an intraoral sensing apparatus when an electronic device 2 is installed in an intraoral instrument 1.
Figure 2:
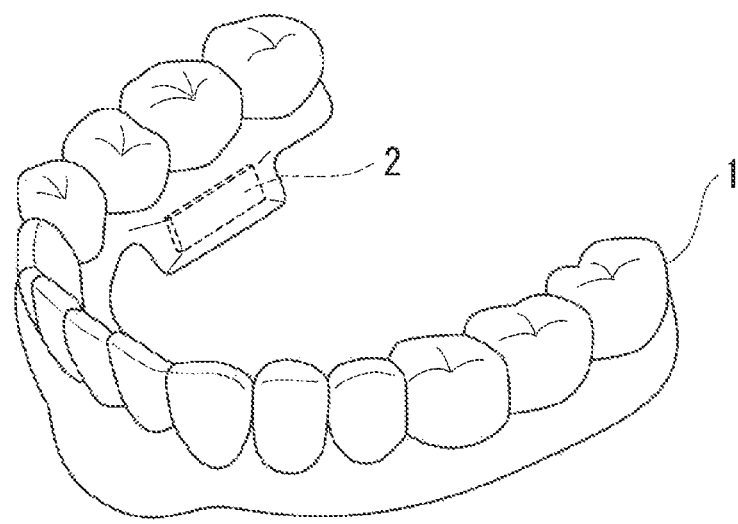
FIG. 2 is a schematic diagram of the intraoral sensing apparatus when the electronic device 2 is installed in the intraoral instrument 1.
Figure 3:
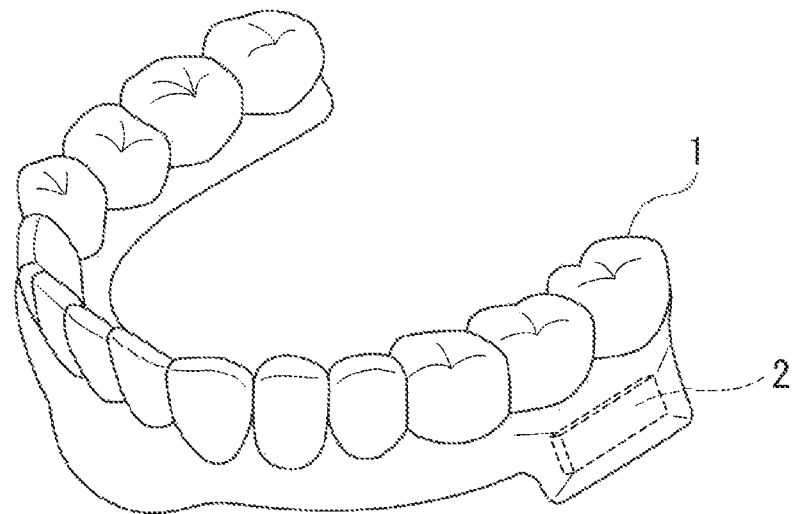
FIG. 3 is a schematic diagram of another intraoral sensing apparatus when the electronic device 2 is installed in the intraoral instrument 1.

In a first specific aspect of the present invention, as shown in FIG. 1, the electronic device 2 completely covered with the first dental resin material 3 is accommodated in a first recess of an intraoral instrument 1, and the second dental resin material 4 is filled into a gap between the electronic device 2 completely covered with the first dental resin material 3 and the first recess such that the electronic device 2 and the intraoral instrument 1 are bonded to each other by the second dental resin material 4. FIG. 2 and FIG. 3 are perspective views of the intraoral instrument 1. In a case where the intraoral instrument is mounted on the teeth and gums, the electronic device 2 may be disposed inside an oral cavity (lingual side), as shown in FIG. 2, or the electronic device 2 may be disposed outside the oral cavity (buccal side), as shown in FIG. 3.

By employing this configuration, the safety of the intraoral sensing apparatus in use is further improved and the intraoral sensing apparatus is more easily manufactured.

Figure 4:
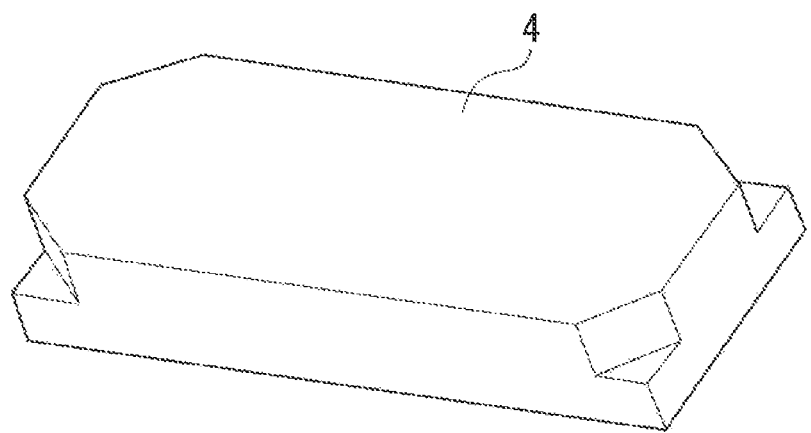
FIG. 4 is a schematic diagram showing a shape of an electronic device which is covered with a second dental resin material 4 and is to be installed in a first recess of the intraoral instrument.
Figure 5:
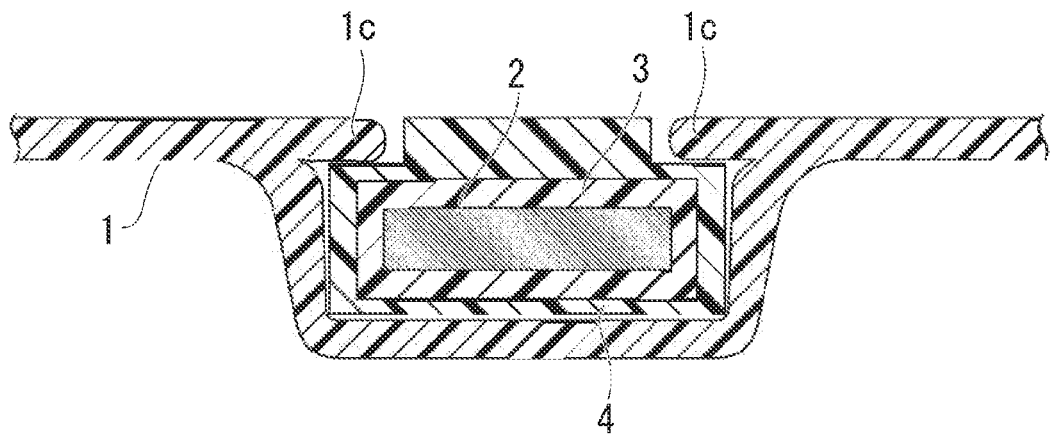
FIG. 5 is a cross-sectional view of a first recess part when the electronic device 2 is installed in the first recess of the intraoral instrument 1.

In a second specific aspect of the present invention, as shown in FIG. 4, the second dental resin material 4, which covers the electronic device 2 completely covered with the first dental resin material 3, is formed such that the thickness at two or more corners of a surface facing a bottom surface which is one of wide surfaces of the first dental resin material 3 is less than a thickness at other portion of the surface; and as shown in FIG. 5, the first recess of the intraoral instrument 1 is provided with first protrusions 1c at positions corresponding to portions where the thickness of the corners of the second dental resin material 4 is less than the thickness of the other portion.

Figure 6:
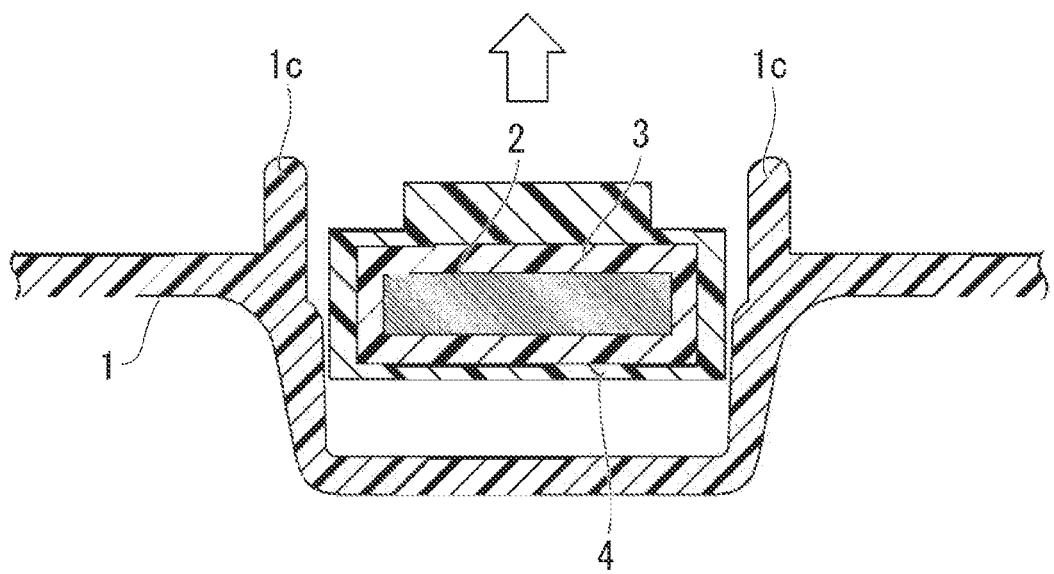
FIG. 6 is a cross-sectional view showing a state when the electronic device 2 installed in the first recess of the intraoral instrument 1 is removed.

By employing this configuration, a force applied to the intraoral instrument 1 when the intraoral instrument 1 is mounted/removed is not directly applied to the electronic device 2, as shown in FIG. 6, and thus a likelihood of the electronic device 2 being broken due to repeated mounting/removal is reduced. In particular, in a case where the intraoral instrument 1 is formed through vacuum press molding, the first recess and the first protrusions 1c can be simultaneously formed and setting of the electronic device 2 can be automatically performed, to improve work efficiency.

Figure 7:
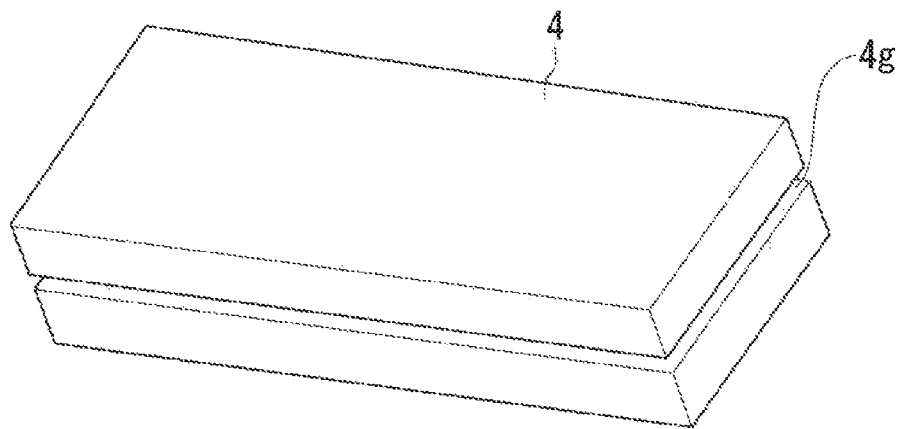
FIG. 7 is a schematic diagram showing another shape of the electronic device which is covered with the second dental resin material 4 and is to be installed in the first recess of the intraoral instrument.
Figure 8:
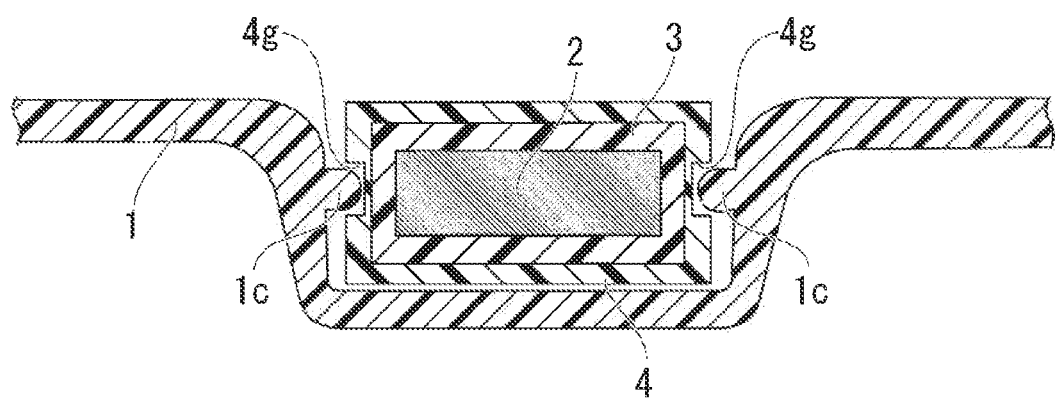
FIG. 8 is a cross-sectional view of another first recess part when the electronic device 2 is installed in the first recess of the intraoral instrument 1.

In a third specific aspect of the present invention, as shown in FIG. 7, the second dental resin material 4 covering the electronic device completely covered with the first dental resin material is provided with a second recess at two or more surfaces corresponding to side surfaces with respect to a bottom surface which is one of wide surfaces of the first dental resin material; and as shown in FIG. 8, the first recess is provided with a first protrusion 1c at a position corresponding to the second recess of the side surfaces of the second dental resin material 4.

By employing this configuration, removal of the electronic device 2 from the intraoral instrument 1 and re-mounting of the electronic device 2 into the intraoral instrument 1 can be more easily performed. In particular, in a case where the intraoral instrument 1 is formed through vacuum press molding, the first recess and the first protrusions 1c can be simultaneously formed and setting of the electronic device 2 can be automatically performed, to improve work efficiency.

Figure 9:
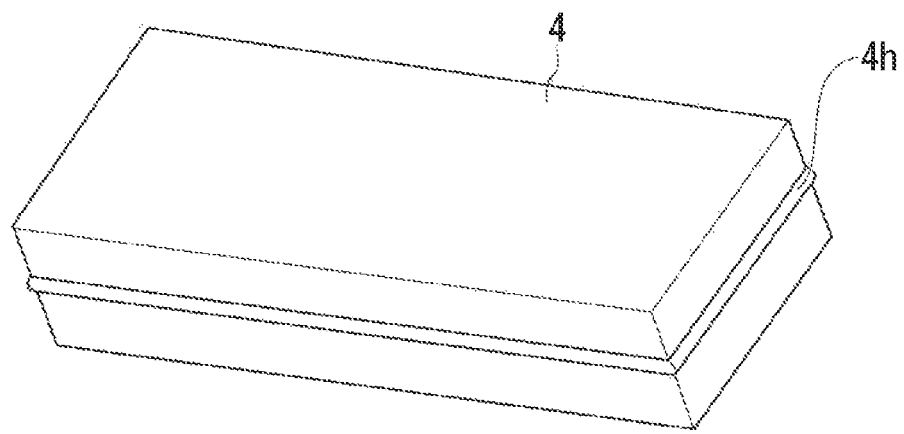
FIG. 9 is a schematic diagram showing another shape of the electronic device which is covered with the second dental resin material 4 and is to be installed in the first recess of the intraoral instrument.
Figure 10:
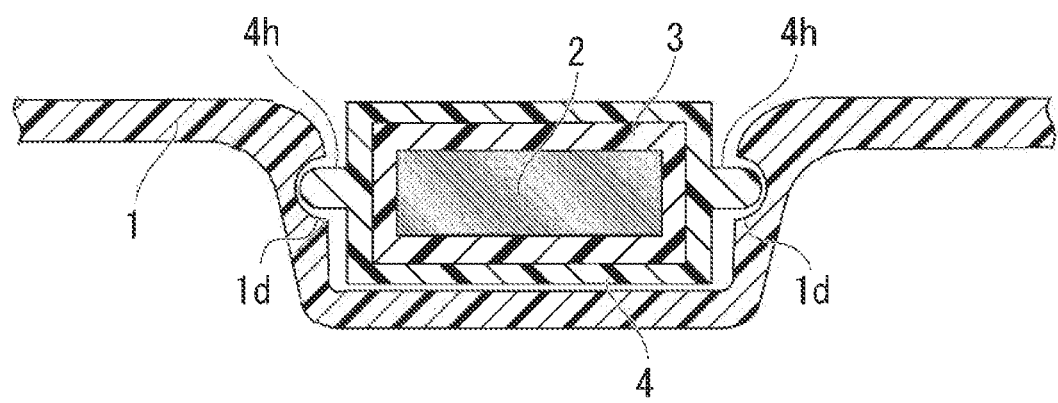
FIG. 10 is a cross-sectional view of another first recess part when the electronic device 2 is installed in the first recess of the intraoral instrument 1.

In a fourth specific aspect of the present invention, as shown in FIG. 9, the second dental resin material 4 covering the electronic device completely covered with the first dental resin material is provided with a second protrusion at two or more surfaces corresponding to side surfaces with respect to a bottom surface which is one of wide surfaces of the first dental resin material; and as shown in FIG. 10, the first recess is provided with a recess 1d at a position corresponding to the second protrusion of the side surfaces of the second dental resin material 4.

By employing this configuration, removal of the electronic device 2 from the intraoral instrument 1 and re-mounting of the electronic device 2 into the intraoral instrument 1 can be more easily performed. In particular, in a case where the intraoral instrument 1 is formed through vacuum press molding, the first recess and the recess 1d can be simultaneously formed and setting of the electronic device 2 can be automatically performed, to improve work efficiency.

Figure 11:
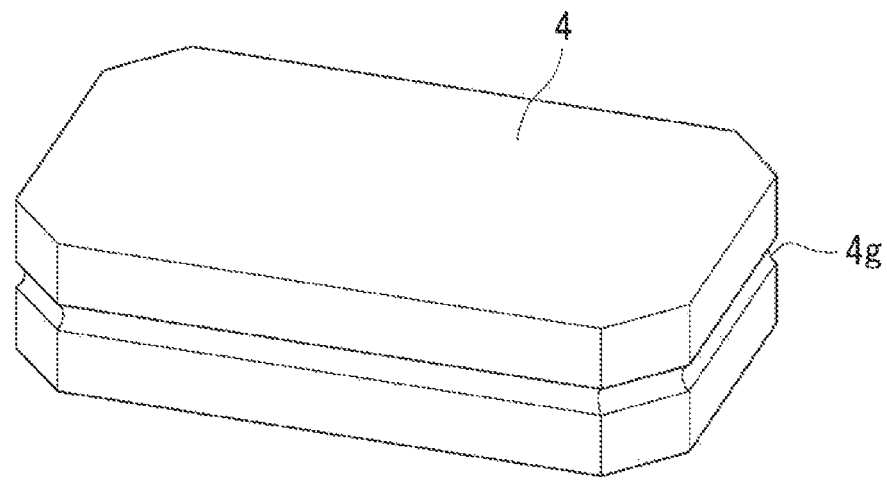
FIG. 11 is a schematic diagram showing another shape of the electronic device which is covered with the second dental resin material 4 and is to be installed in the first recess of the intraoral instrument.
Figure 12:
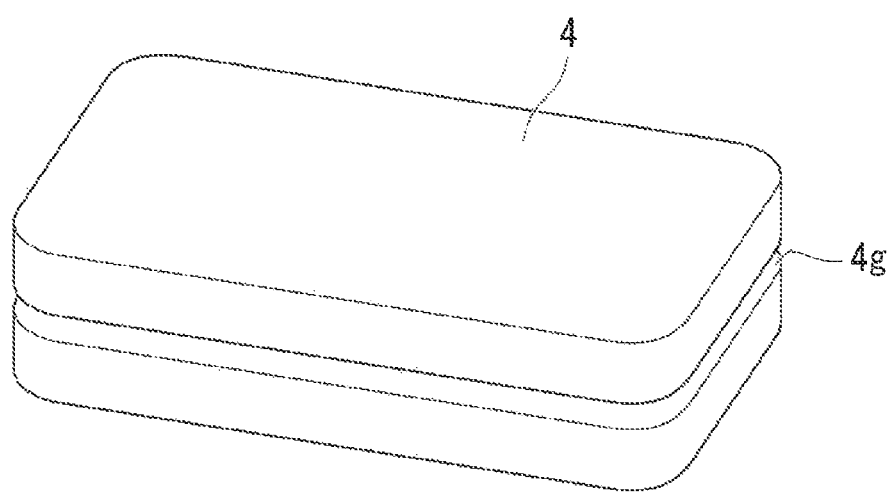
FIG. 12 is a schematic diagram showing another shape of the electronic device which is covered with the second dental resin material 4 and is to be installed in the first recess of the intraoral instrument.
Figure 13:
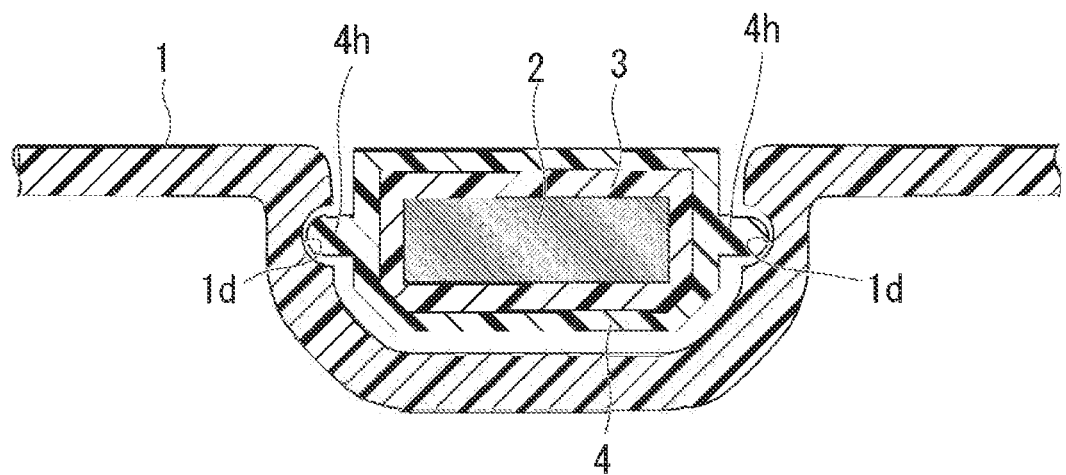
FIG. 13 is a cross-sectional view of another first recess part when the electronic device 2 is installed in the first recess of the intraoral instrument 1.
Figure 14:
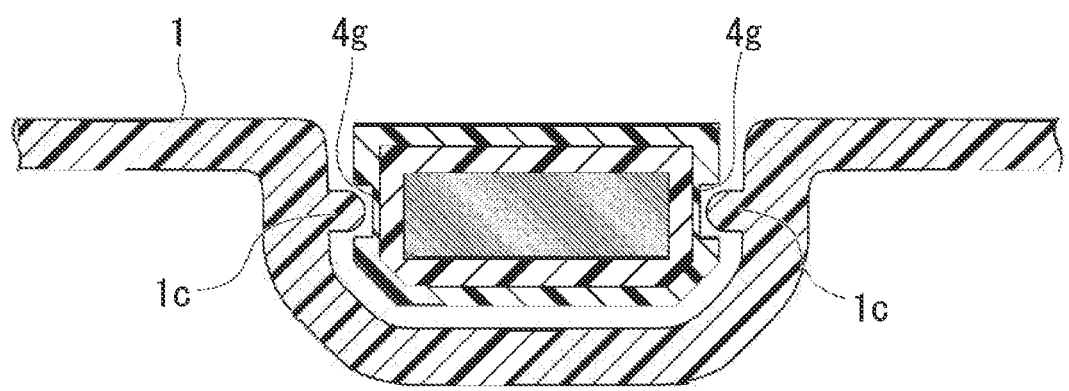
FIG. 14 is a cross-sectional view of another first recess part when the electronic device 2 is installed in the first recess of the intraoral instrument 1.

In the above-described second and third specific aspects of the present invention, the shape of the second dental resin material 4 is not limited to an approximately rectangular parallelepiped shape and the corners thereof may be rounded or cut off, as shown in FIG. 11 or FIG. 12. In addition, corners in contact with the bottom of the first recess may be cut off or rounded, as shown in FIG. 13 or FIG. 14.

[Intraoral Sensing Apparatus]

The intraoral sensing apparatus includes the electronic device 2, the intraoral instrument 1, the first dental resin material 3, and the second dental resin material 4.

<Electronic Device>

Figure 16:
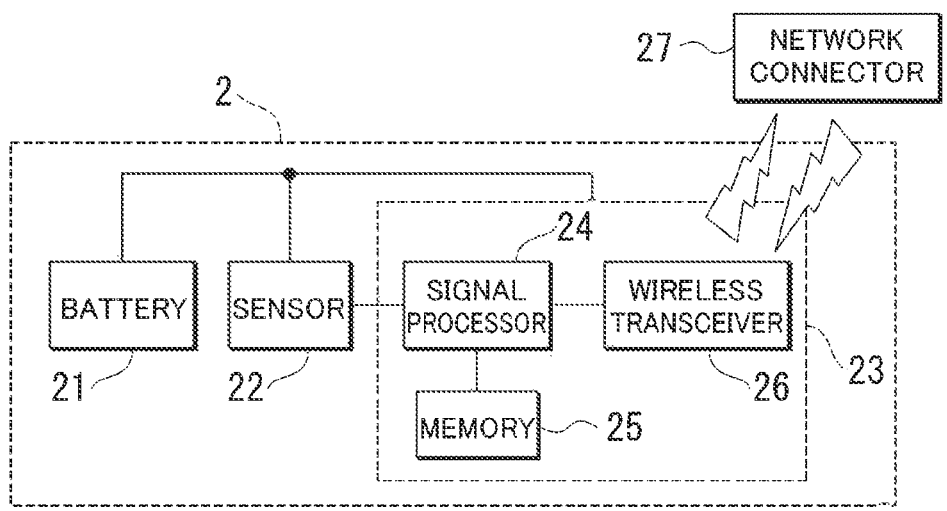
FIG. 16 is a schematic block diagram showing a circuit configuration of the electronic device 2.
Figure 17:
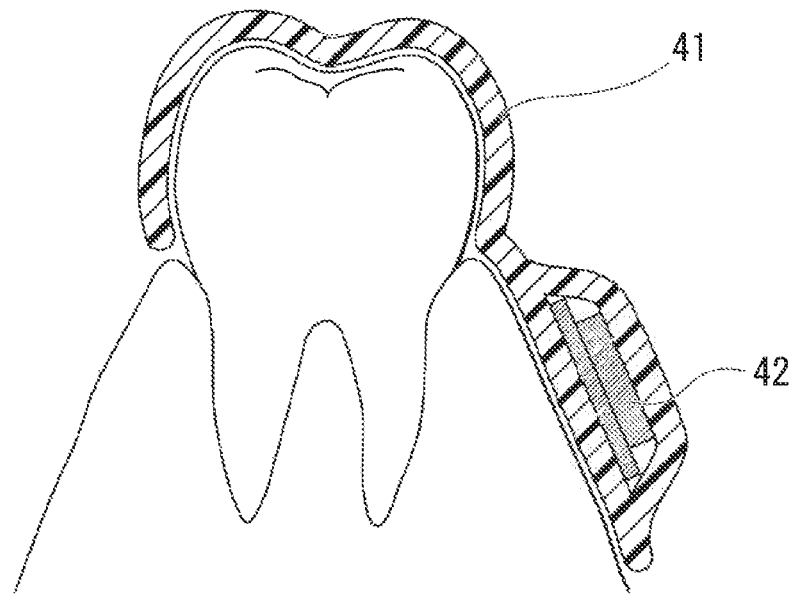
FIG. 17 is a cross-sectional view of a conventional intraoral sensing apparatus when an electronic device 42 is installed in an intraoral instrument 41.

As shown in FIG. 16, the electronic device 2 includes a wireless module unit 23 in which a wireless transceiver 26, a signal processor 24, and a memory 25 are combined, a sensor 22, and a battery 21 and is completely covered with the first dental resin material 3 in a state in which it is mounted on a circuit board.

The electronic device 2 includes the wireless module unit 23 in which the wireless transceiver 26, the signal processor 24, and the memory 25 are combined, the sensor 22, and the battery 21 and is embedded in an orthodontic instrument, a denture, or a dental implant.

The wireless transceiver 26 serves to transmit digital data from sensing in an oral cavity to a network connector 27 outside the oral cavity or receive a command transmitted from the network connector 27 to the electronic device 2.

The signal processor 24 includes a microcomputer and an AD converter, serves to convert sensing data sent from the sensor 22 into digital data and store the digital data in the memory 25, serves to convert digital data stored in the memory 25 into transmittable data, and serves to analyze a command sent from the network connector 27 and control operations of the sensor 22 and the wireless transceiver 26.

The sensor 22 includes at least one selected from a group consisting of a temperature sensor, an acceleration sensor, a gyro sensor, a pressure sensor, a strain sensor, a pulse wave sensor that measures pulse waves using light, a pulse oximeter that measures a blood oxygen concentration using light, a heart rate sensor that measures a heart rate using light, and a laser sensor that measures a blood flow using laser light and acquires various types of physical information and biometric information.

The battery 21 includes a primary battery or a secondary battery and supplies power to the wireless transceiver 26, the signal processor 24, the memory 25, and the sensor 22.

These circuit blocks are provided in such a manner that the battery 21, the sensor 22, the signal processor 24, the wireless transceiver 26, and the memory 25 are mounted on a thin circuit board or a flexible board. In general, the wireless transceiver 26, the signal processor 24, and the memory 25 are integrated and provided through a chip in many cases. In addition, the electronic device 2 has the battery 21, the sensor 22, the signal processor 24, the memory 25, and the wireless transceiver 26 mounted on a thin circuit board or a flexible board.

The electronic device 2 is covered with the first dental resin material 3, the outside thereof is additionally covered with the second dental resin material 4, and then the electronic device 2 is installed in the intraoral instrument, and thus infiltration of moisture into the electronic device 2 can be prevented. Even if the second dental resin material 4 cracks, double safety is secured because the electronic device 2 is covered with the first dental resin material 3 that is soft.

The wireless module unit 23 mounted in the electronic device 2 need not necessarily perform data exchange with the outside in a wireless manner, and an electronic device that performs data exchange in a wired manner may be employed. However, in the case of an electronic device that performs data exchange in a wired manner, it is necessary to waterproof a connector part that connects the electronic device 2 and the network connector 27. The connector part employs a mechanism such as a lid which is opened when data is read and closed when installed in an oral cavity. Accordingly, the way of transmitting and receiving data wirelessly has a merit of being simple in a waterproof structure.

By using a temperature sensor as the sensor 22, it is possible to not only measure a time for which the intraoral instrument is mounted and use the measured time for an intraoral orthodontic treatment, but also monitor change in a daily body temperature.

By using an acceleration sensor/gyro sensor as the sensor 22, it is possible to not only count the number of times of mastication, but also perform measurement of the number of steps, measurement of an amount of action, measurement of a motion of a jaw, and measurement of bruxism (gnashing).

By using a pressure sensor/strain sensor as the sensor 22, it is possible to not only measure a force applied to a tooth, a denture, or a dental implant but also perform measurement of a force applied by the intraoral instrument to a tooth, measurement of bruxism (gnashing), measurement of a biting force, measurement of the number of times of mastication, and measurement of a time for which the intraoral instrument is mounted.

<Intraoral Instrument>

As the intraoral instrument 1, for example, an orthodontic instrument, a denture, or a dental implant may be conceived.

In the case of an orthodontic instrument, it is desirable that the intraoral instrument 1 be formed of a thermoplastic polymeric compound and it is more desirable that the intraoral instrument 1 be formed of any thermoplastic polymeric compound selected from a group consisting of a polyethylene material, a polyurethane material, and an acrylic resin.

In a case where the electronic device is mounted in the intraoral instrument, as shown in FIG. 1 to FIG. 3, it is desirable that the intraoral instrument be formed through press molding by pressing an intraoral instrument manufacturing material onto a tooth mold matching the teeth and gums of a user, at which the intraoral sensing apparatus is scheduled to be mounted, or be molded into a tooth mold and gum mold shape using a 3D printer, and it is more desirable that the intraoral instrument be formed through press molding by pressing the material onto a tooth mold matching the teeth and gums of a user, at which the intraoral sensing apparatus is scheduled to be mounted.

It is desirable that the intraoral instrument manufacturing material be a sheet or a film of the aforementioned thermoplastic polymeric compound.

A recess is provided in a part of the intraoral instrument 1 and the electronic device 2 is disposed in the recess. Although the electronic device 2 may be disposed in any of a place corresponding to a sidewall of a crown part and a place corresponding to a gum, it is desirable to dispose the electronic device 2 in a place corresponding to a gum shown in FIG. 1 in consideration of occlusion of upper teeth and lower teeth. In addition, in the case of a pulse wave sensor that measures pulse waves using light, a pulse oximeter that measures a blood oxygen concentration using light, a heart rate sensor that measures a heart rate using light, and a laser sensor that measures a blood flow using laser light, it is desirable to dispose the electronic device 2 in a place corresponding to a gum in order to acquire information from blood vessels of the gum.

Further, in a case where the intraoral instrument 1 is equipped with the aforementioned sensors using light or laser, the intraoral instrument 1 is formed of a material capable of transmitting light with any wavelength in a range of 400 nm to 1000 nm because transmission of light is required.

In the first specific aspect, as shown in FIG. 1, the circumference of the electronic device 2 is completely covered with the first dental resin material 3, the circumference of the first dental resin material 3 is additionally completely covered with the second dental resin material 4, and the second dental resin material 4 is filled in the recess of the intraoral instrument 1 to bond the electronic device 2 to the intraoral instrument 1.

In the second specific aspect, as shown in FIG. 4, a structure is employed in which a thickness of the second dental resin material 4 at two or more corners of a surface facing a bottom surface which is one of wide surfaces of the first dental resin material is less than a thickness at other portion. In addition, as shown in FIG. 5, since the electronic device 2 is fixed by portions where the thickness of the corners of the second dental resin material 4 is less than the thickness of other portions and the first protrusions 1c of the intraoral instrument 1, even when a strong force is applied to the intraoral instrument 1, the force is not directly applied to the electronic device 2. Accordingly, it is possible to avoid a problem that a force is applied to the electronic device 2 to break the electronic device 2 when the intraoral instrument 1 is mounted/removed. In addition, in a case where only one position where a corner of the second dental resin material 4 is thin is formed, the electronic device 2 is considerably highly likely to be detached, which is not desirable. The electronic device 2 is prevented from being detached even when the intraoral instrument 1 is mounted/removed by forming thin corners at two or more positions, if possible, four positions. FIG. 6 is a schematic diagram showing a state when the electronic device 2 covered with the first dental resin material 3 and the second dental resin material 4 is removed from the intraoral instrument 1. Since the first protrusions 1c of the intraoral instrument 1 are deformed when the electronic device 2 is taken out in a direction of an arrow, it is possible to easily take out the electronic device 2 covered with the first dental resin material 3 and the second dental resin material 4 from the intraoral instrument 1.

In the third specific aspect, as shown in FIG. 7, a structure is employed in which the second dental resin material 4 is provided with the second recess 4g at two or more of the surfaces corresponding to the side surfaces with respect to a bottom surface which is one of wide surfaces of the first dental resin material. In addition, even when a strong force is applied to the intraoral instrument 1, the force is not directly applied to the electronic device 2 because the electronic device 2 is fixed by the second recess 4g formed on the side of the second dental resin material 4 and the first protrusions 1c of the intraoral instrument, as shown in FIG. 8. Accordingly, it is possible to avoid a problem that a force is applied to the electronic device 2 to break the electronic device 2 when the intraoral instrument 1 is mounted/removed. In addition, in a case where the second recess 4g is formed in only one surface of the side, the electronic device 2 is considerably highly likely to be detached, which is not desirable. The electronic device 2 is prevented from being detached even when the intraoral instrument 1 is mounted/removed by forming the second recess 4g in two or more surfaces, if possible, four surfaces of the side. It is desirable that the second recess 4g be parallel to the bottom surface.

In the fourth specific aspect, as shown in FIG. 9, a structure is employed in which the second dental resin material 4 is provided with the second protrusion 4h at two or more of the surfaces corresponding to the side surfaces with respect to a bottom surface which is one of wide surfaces of the first dental resin material. In addition, even when a strong force is applied to the intraoral instrument 1, the force is not directly applied to the electronic device 2 because the electronic device 2 is fixed by the second protrusion 4h formed on the side of the second dental resin material 4 and a recess 1d of the intraoral instrument, as shown in FIG. 10. Accordingly, it is possible to avoid a problem that a force is applied to the electronic device 2 to break the electronic device 2 when the intraoral instrument 1 is mounted/removed. In addition, in a case where the second protrusion 4h is formed only on one surface of the side, the electronic device 2 is considerably highly likely to be detached, which is not desirable. The electronic device 2 is prevented from being detached even when the intraoral instrument 1 is mounted/removed by forming the second protrusion 4h on two or more surfaces, if possible, four surfaces of the side. It is desirable that the second protrusion 4h be parallel to the bottom surface.

In the case of the second specific aspect (FIG. 4), the third specific aspect (FIG. 7), or the fourth specific aspect (FIG. 9), a method of forming the intraoral instrument 1 of a thermoplastic polymeric compound such as a polyethylene material, a polyurethane material, or acrylic resin, and pressing the intraoral instrument 1 onto a tooth mold formed using a plaster or a 3D printer is suitable. When the electronic device 2 covered with the second dental resin material 4 shown in FIG. 4, FIG. 7, or FIG. 9 is placed at a position on the tooth mold at which the electronic device 2 is desired to be installed, and a thermoplastic polymeric compound sheet or film is molded through vacuum pressing, the thermoplastic polymeric compound enters into the positions at which corners are thin and the first recess and thus the first protrusions 1c of the intraoral instrument 1 as shown in FIG. 5 or FIG. 8, or the recess 1d of the intraoral instrument 1 as shown in FIG. 10 can be automatically formed.

Although it is necessary to set the electronic device 2 in the first recess of the intraoral instrument 1 when the intraoral instrument 1 is manufactured using a 3D printer, in a case where vacuum pressing is performed for the electronic device 2 in the shape shown in FIG. 4, FIG. 7, or FIG. 9, work efficiency is promoted because the process for setting the electronic device 2 can be reduced.

A position at which the electronic device 2 is installed in the intraoral instrument 1 may be any of an upper jaw and a lower jaw, or any of the inside (lingual side) or the outside (buccal side) in the oral cavity.

Figure 15:
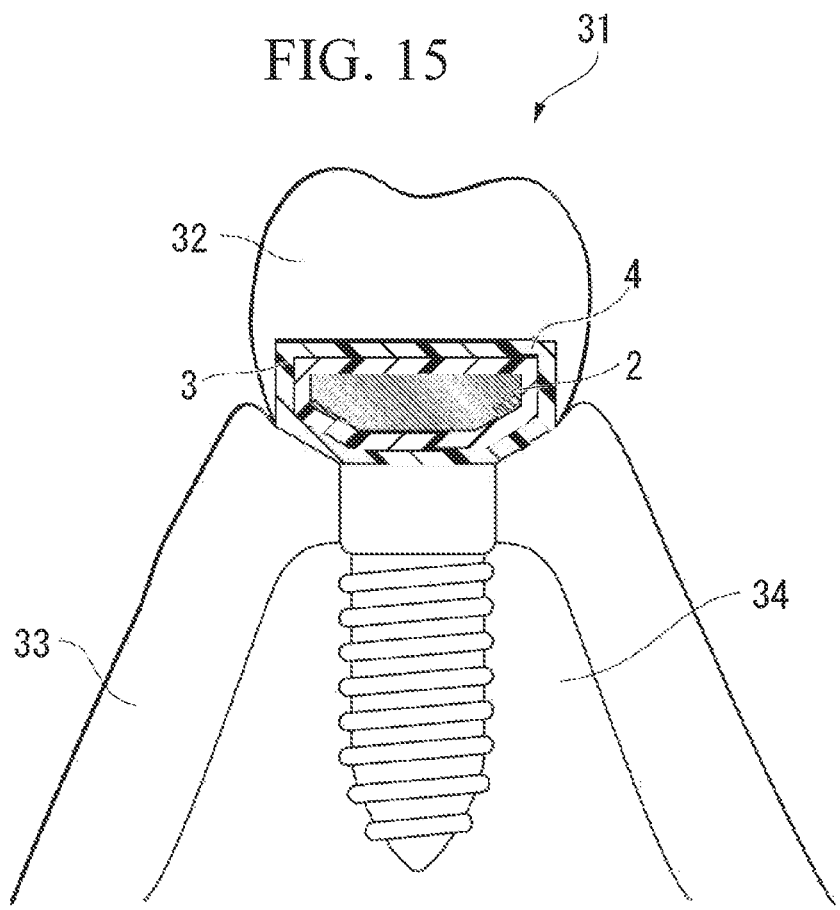
FIG. 15 is a cross-sectional view of the intraoral sensing apparatus when the electronic device 2 is installed in an implant denture 32.

In a case where the electronic device 2 is mounted in a denture or a dental implant, it is desirable to install the electronic device 2 in the denture (implant denture 32), as shown in FIG. 15. Although FIG. 15 illustrates an example of a dental implant embedded in an alveolar bone 34, the same applies to the denture. It is desirable that the electronic device 2 be completely doubly covered with the first dental resin material 3 and the second dental resin material 4 and installed inside a denture or the implant denture 32.

In the case of a pulse wave sensor that measures pulse waves using light, a pulse oximeter that measures a blood oxygen concentration using light, a heart rate sensor that measures a heart rate using light, and a laser sensor that measures a blood flow using laser light, information is acquired from blood vessels of a gum, and thus it is desirable to install the electronic device 2 in a place corresponding to a gum 33. Further, in a case where the aforementioned sensors using light or laser are mounted, a part of the denture or the implant denture is formed of a material capable of transmitting light with any wavelength in a range of 400 nm to 1000 nm for transmission of light.

<First Dental Resin Material>

The first dental resin material 3 is obtained, for example, by adding butyl phthalate as a plasticizing agent to a silicone resin or a methacrylate having polydimethylsiloxane as a main ingredient and polymerizing and curing it. As the aforementioned silicone resin, a condensation silicon rubber or an addition silicon rubber is exemplified. The first dental resin material 3 is not limited to the aforementioned ones and other plastics may also be used. A silicone resin is desirable as the first dental resin material 3.

The silicone resin has a weak adhesion to the electronic device 2 and thus can be easily removed. Accordingly, in a case where the electronic device 2 is reused, cleanness can be always maintained by newly exchanging the silicone resin. In addition, since the silicone resin has a weak adhesion to the second dental resin material 4 which will be described later, the electronic device 2 can be easily detached from the intraoral instrument 1.

<Second Dental Resin Material>

For example, the second dental resin material 4 is a material obtained by polymerizing and curing methyl methacrylate and polymethyl methacrylate, a material having 2,2-bis(4-(3-methacryloxy-2-hydroxypropoxy)phenyl)propane, urethane dimethacrylate, and triethylene glycol dimethacrylate as main ingredients, a material obtained by polymerizing and curing polymethyl methacrylate, 4-methacryloyloxy ethyltrimellitate anhydride, and tri-n-butylborane, a polyethylene resin, a polyurethane resin, or an acrylic resin. The second dental resin material 4 is not limited to the aforementioned materials, and other plastics may also be used. As the second dental resin material 4, a material obtained by polymerizing and curing methyl methacrylate and polymethyl methacrylate is desirable because it has high coverage of covering the electronic device 2 and can prevent moisture from infiltrating into the device.

Since a material obtained by polymerizing and curing methyl methacrylate and polymethyl methacrylate or a dental resin material obtained by polymerizing and curing polymethyl methacrylate, 4-methacryloyloxy ethyltrimellitate anhydride, and tri-n-butylborane is a type of polymerization and curing of a solution and powder, the dental resin material does not run off and can fill the gap between the electronic device 2 and the intraoral instrument. A polymerization procedure is performed in such a manner that a liquid is applied to a brush or a gauntlet first, and then powder is applied to the brush or the gauntlet. Accordingly, the viscosity of the dental resin material is improved and thus the dental resin material can be placed in the gap between the electronic device 2 and the intraoral instrument.

The second dental resin material 4 is softer than the first dental resin material 3 and has a strong adhesion to the intraoral instrument 1 and thus can fix the electronic device 2 to the intraoral instrument 1 with a strong holding force. In addition, the first dental resin material 3 is harder than the second dental resin material 4 and is suitable for protecting the electronic device 2 from an external force.

[Method of Manufacturing Intraoral Sensing Apparatus]

Figure 18:
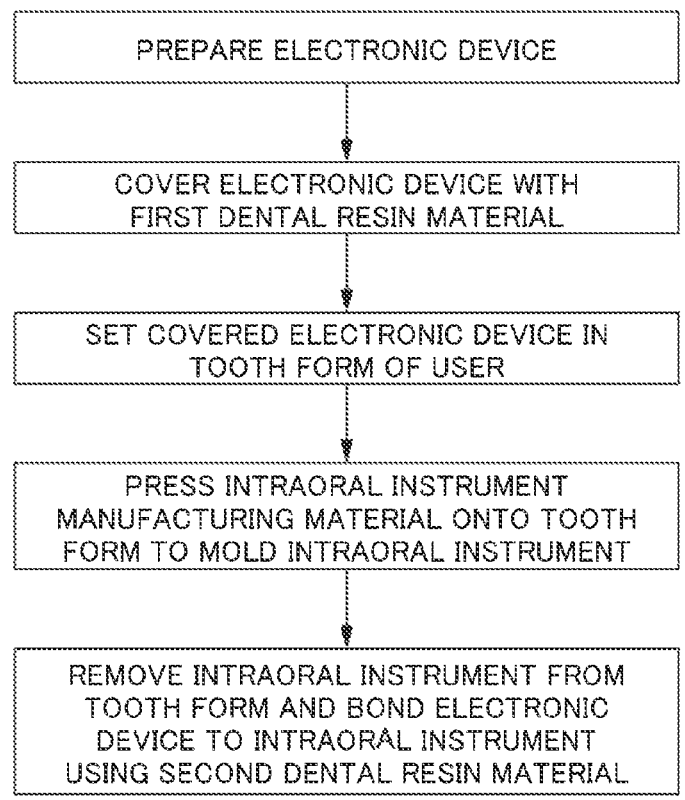
FIG. 18 is a process flowchart showing a method of manufacturing an intraoral sensing apparatus.

As shown in FIG. 18, an intraoral sensing apparatus according to the first specific aspect of the present invention can be manufactured by, for example, preparing the electronic device 2 equipped with electronic components mounted on a circuit board, completely covering the electronic device 2 with the first dental resin material 3, preparing a tooth mold matching the teeth and gums of a user at which the intraoral sensing apparatus is scheduled to be mounted, placing the electronic device 2 covered with the first dental resin material 3 in the tooth mold, performing press molding by pressing the tooth mold onto a material for manufacturing the intraoral instrument to mold the intraoral instrument 1 having a first recess in which the electronic device 2 covered with the first dental resin material 3 will be accommodated, removing the intraoral instrument 1 from the tooth mold in a state in which the electronic device 2 covered with the first dental resin material 3 is accommodated in the first recess, and covering the electronic device 2 covered with the first dental resin material 3 with the second dental resin material 4 such that the second dental resin material 4 completely covers the first dental resin material 3 and is bonded to the inside of the first recess of the intraoral instrument 1.

Figure 19:
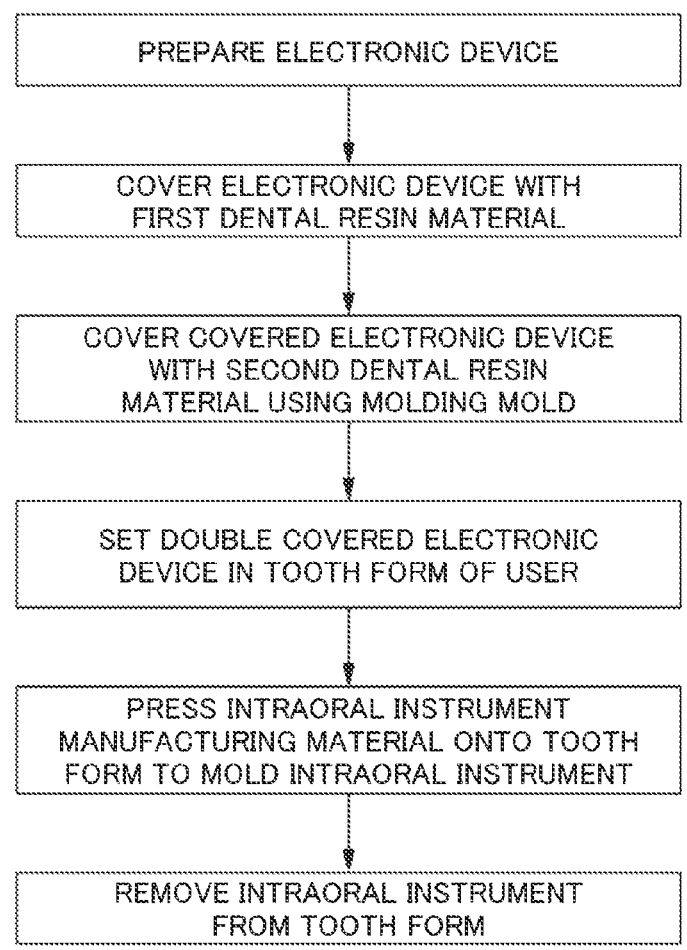
FIG. 19 is a process flowcharts showing another method of manufacturing an intraoral sensing apparatus.

As shown in FIG. 19, an intraoral sensing apparatus according to the second specific aspect of the present invention can be manufactured by, for example, preparing the electronic device 2 equipped with electronic components mounted on a circuit board, completely covering the electronic device 2 with the first dental resin material 3, covering the electronic device 2 covered with the first dental resin material 3 with the second dental resin material 4 such that a thickness of the second dental resin material 4 at two or more corners of a surface facing a bottom surface which is one of wide surfaces of the first dental resin material is less than a thickness at other portion, preparing a tooth mold matching the teeth and gums of a user at which the intraoral sensing apparatus is scheduled to be mounted, placing the electronic device 2 covered with the first dental resin material 3 and the second dental resin material 4 in the tooth mold, performing press molding by pressing the tooth mold onto a material for manufacturing the intraoral instrument to mold the intraoral instrument 1 having the first recess in which the electronic device 2 covered with the first dental resin material 3 and the second dental resin material 4 will be accommodated, and removing the intraoral instrument 1 from the tooth mold in a state in which the electronic device 2 covered with the first dental resin material 3 and the second dental resin material 4 is accommodated in the first recess.

As shown in FIG. 19, an intraoral sensing apparatus according to the third specific aspect of the present invention can be manufactured by, for example, preparing the electronic device 2 equipped with electronic components mounted on a circuit board, completely covering the electronic device 2 with the first dental resin material 3, covering the electronic device 2 covered with the first dental resin material 3 with the second dental resin material 4 such that the second dental resin material 4 completely covers the first dental resin material 3 and a second recess is provided at two or more of the surfaces corresponding to the side surfaces with respect to a bottom surface which is one of wide surfaces of the first dental resin material 3, preparing a tooth mold matching the teeth and gums of a user at which the intraoral sensing apparatus is scheduled to be mounted, placing the electronic device 2 covered with the first dental resin material 3 and the second dental resin material 4 in the tooth mold, performing press molding by pressing the tooth mold onto a material for manufacturing the intraoral instrument to mold the intraoral instrument 1 having the first recess in which the electronic device 2 covered with the first dental resin material 3 and the second dental resin material 4 will be accommodated, and removing the intraoral instrument 1 from the tooth mold in a state in which the electronic device 2 covered with the first dental resin material 3 and the second dental resin material 4 is accommodated in the first recess. It is desirable that the second recess be provided in parallel to the bottom surface.

As shown in FIG. 19, an intraoral sensing apparatus according to the fourth specific aspect of the present invention can be manufactured by, for example, preparing the electronic device 2 equipped with electronic components mounted on a circuit board, completely covering the electronic device 2 with the first dental resin material 3, covering the electronic device 2 covered with the first dental resin material 3 with the second dental resin material 4 such that the second dental resin material 4 completely covers the first dental resin material 3 and a second protrusion is provided at two or more of the surfaces corresponding to the side surfaces with respect to a bottom surface which is one of wide surfaces of the first dental resin material 3, preparing a tooth mold matching the teeth and gums of a user at which the intraoral sensing apparatus is scheduled to be mounted, placing the electronic device 2 covered with the first dental resin material 3 and the second dental resin material 4 in the tooth mold, performing press molding by pressing the tooth mold onto a material for manufacturing the intraoral instrument to mold the intraoral instrument 1 having the first recess in which the electronic device 2 covered with the first dental resin material 3 and the second dental resin material 4 will be accommodated, and removing the intraoral instrument 1 from the tooth mold in a state in which the electronic device 2 covered with the first dental resin material 3 and the second dental resin material 4 is accommodated in the first recess. It is desirable that the second protrusion be provided in parallel to the bottom surface.

The intraoral instrument 1, the electronic device 2, the first dental resin material 3, and the second dental resin material 4 are the same as those described with respect to the intraoral sensing apparatus of the present invention and desirable ones are also the same as those described with respect to the intra-oral sensing apparatus of the present invention.

[Effects]

In the intraoral sensing apparatus of the present invention, the electronic device 2 is completely covered with the first dental resin material 3, and thus the electronic device 2 is not detached when it is used even when adhesion between the first dental resin material 3 and the electronic device 2 is considerably weak.

The electronic device 2 can be easily detached from the intraoral instrument 1 even when the electronic device 2 is reused through charging or the like by using a silicone resin as the first dental resin material 3, and the electronic device 2 is not damaged and easily reused because the silicone resin can also be cleanly removed.

Although a sufficient sterilization work is necessary in a case where the electronic device 2 put in an oral cavity is reused, the electronic device 2 can be easily cleaned because the silicone resin is thrown away after used once in the intraoral sensing apparatus of the present invention.

Since the electronic device 2 is covered with the first dental resin material 3 and the second dental resin material 4 when it is used in an oral cavity, the waterproofness of the electronic device 2 is improved.

Since the electronic device 2 is covered with the first dental resin material 3 and the second dental resin material 4 when it is used in an oral cavity, safety for a human body is secured if any of the first dental resin material 3 and the second dental resin material 4 cracks because the electronic device 2 is protected by the other material.

Since a part of the intraoral instrument 1 is recessed and the electronic device 2 is mounted inside the intraoral sensing apparatus of the present invention, a manufacturing process is simple.

It is possible to reduce the thickness of the material of the intraoral instrument 1 because a part of the intraoral instrument 1 is recessed and the electronic device 2 is mounted therein. For example, in a case where the intraoral instrument 1 is an orthodontic instrument, it is also possible to finely control a force applied to a row of teeth.

The second dental resin material 4 used to mount the electronic device 2 in the intraoral instrument 1 is a material obtained by polymerizing and curing a solution and powder and thus it does not run off. Accordingly, when the first dental resin material 3 is covered with the second dental resin material 4, a brush-on technique of impregnating a brush with a liquid ingredient first and then applying powder to the brush to plaster it to the circumference of the first dental resin material 3, or a method of sprinkling a liquid ingredient and power each other can be used.

In the second specific aspect, since the electronic device 2 is fixed by portions at which a thickness of corners is less than a thickness of the other portion and the first protrusions 1c of the intraoral instrument 1 through the second dental resin material 4, even when a strong force is applied to the intraoral instrument, the force is not directly applied to the electronic device 2. Accordingly, it is possible to avoid a problem that a force is applied to the electronic device 2 to damage the electronic device 2 when the intraoral instrument 1 is mounted/removed.

In the third specific aspect, since the electronic device 2 is fixed by the second recess of the second dental resin material 4 and the first protrusions 1c of the intraoral instrument 1 through the second dental resin material 4, even when a strong force is applied to the intraoral instrument, the force is not directly applied to the electronic device 2. Accordingly, it is possible to avoid a problem that a force is applied to the electronic device 2 to damage the electronic device 2 when the intraoral instrument 1 is mounted/removed. When the electronic device 2 is mounted in a structure in which a part of the intraoral instrument 1 is recessed and the first protrusions 1c are additionally provided through a method of molding the intraoral instrument 1 through vacuum pressing, the first protrusions 1c can be automatically formed and setting of the electronic device 2 can also be automatically performed to improve work efficiency.

In the fourth specific aspect, since the electronic device 2 is fixed by the second protrusion of the second dental resin material 4 and the recess 1d of the intraoral instrument 1 through the second dental resin material 4, even when a strong force is applied to the intraoral instrument, the force is not directly applied to the electronic device 2. Accordingly, it is possible to avoid a problem that a force is applied to the electronic device 2 to damage the electronic device 2 when the intraoral instrument 1 is mounted/removed. When the electronic device 2 is mounted in a structure in which a part of the intraoral instrument 1 is recessed and the recess 1d is additionally provided through a method of molding the intraoral instrument 1 through vacuum pressing, the recess 1d can be automatically formed and setting of the electronic device 2 can also be automatically performed to improve work efficiency.

It is easy to extract sensed information to the outside by including the wireless transceiver 26 in the electronic device 2.

It is possible to not only measure a time for which the intraoral instrument 1 mounted and use the time for an intraoral orthodontic treatment but also monitor change in a daily body temperature by using a temperature sensor as the sensor 22.

It is possible to not only count the number of times of mastication but also perform one or more selected from a group consisting of measurement of the number of steps, measurement of an amount of action, measurement of a motion of a jaw, and measurement of bruxism (gnashing) by using an acceleration sensor/gyro sensor as the sensor 22.

It is possible to not only measure a force applied to a tooth, a denture, or a dental implant but also perform one or more selected from a group consisting of measurement of a force applied by the intraoral instrument 1 to a tooth, measurement of bruxism (gnashing), measurement of a biting force, measurement of the number of times of mastication, and measurement of a time for which the intraoral instrument is mounted by using a pressure sensor/strain sensor as the sensor 22.

Meanwhile, "silicon resin" in the specification of Japanese Patent Application No. 2020-044440 means "silicone resin" in the specification of the present application.

What is claimed is:

1. An intraoral sensing apparatus configured to be installed in an oral cavity, comprising:
    an electronic device equipped with electronic components mounted on a circuit board;
    a first dental resin material which completely covers the electronic device;
    a second dental resin material which completely covers the first dental resin material; and
    an intraoral instrument having a first recess in which the electronic device covered with the first dental resin material and the second dental resin material is accommodated,
    wherein:
        a thickness of the second dental resin material at two or more corners of a surface facing a bottom surface which is one of wide surfaces of the first dental resin material is less than a thickness at other portion of the surface of the second dental resin material, wherein the other portion of the surface is different from the two or more corners of the surface, and
        the first recess is provided with first protrusions at positions corresponding to portions where the thickness of the corners of the second dental resin material is less than the thickness of the other portion.

2. The intraoral sensing apparatus according to claim 1, wherein
    the second dental resin material bonds the electronic device covered with the first dental resin material to an inside of the first recess.

3. The intraoral sensing apparatus according to claim 1, wherein:
    the second dental resin material is provided with a second protrusion at two or more surfaces corresponding to side surfaces with respect to a bottom surface which is one of wide surfaces of the first dental resin material; and
    the first recess is provided with a recess at a position corresponding to the second protrusion of the side surfaces of the second dental resin material.

4. The intraoral sensing apparatus according to claim 3, wherein
    the second protrusion is parallel to the bottom surface.

5. The intraoral sensing apparatus according to claim 1, wherein
    the intraoral instrument is formed of a thermoplastic polymeric compound.

6. The intraoral sensing apparatus according to claim 1, wherein
    the first dental resin material has a polydimethylsiloxane as a main ingredient.

7. The intraoral sensing apparatus according to claim 1, wherein
    the first dental resin material is obtained by adding butyl phthalate as a plasticizing agent to a methacrylate and polymerizing and curing the resultant material.

8. The intraoral sensing apparatus according to claim 1, wherein
    the second dental resin material is obtained by polymerizing and curing methyl methacrylate and polymethyl methacrylate.

9. The intraoral sensing apparatus according to claim 8, wherein
    the second dental resin material is formed by a brush-on technique of impregnating a brush with a liquid ingredient first and then applying powder to the brush to plaster the liquid ingredient with the powder to the circumference of the first dental resin material.

10. The intraoral sensing apparatus according to claim 8, wherein
    the second dental resin material is formed by alternately sprinkling a liquid ingredient and a power thereon.

11. The intraoral sensing apparatus according to claim 1, wherein
    the second dental resin material has at least one selected from a group consisting of 2,2-bis(4-(3-methacryloxy-2-hydroxypropoxy)phenyl) propane, urethane dimethacrylate, and triethylene glycol dimethacrylate as a main ingredient.

12. The intraoral sensing apparatus according to claim 1, wherein
    the second dental resin material is obtained by polymerizing and curing polymethyl methacrylate, 4-methacryloyloxy ethyltrimellitate anhydride, and tri-n-butylborane.

13. The intraoral sensing apparatus according to claim 1, wherein
    the second dental resin material is any one selected from a group consisting of a polyethylene resin, a polyurethane resin, or an acrylic resin.

14. The intraoral sensing apparatus according to claim 1, wherein
    the electronic device comprises:
    a sensor which is configured to sense a biometric information;
    a battery which is configured to supply a power to the sensor;
    a signal processor which is configured to receive a power supply from the battery and generate a digital data on the basis of an output signal from the sensor;
    a memory which is configured to store the digital data; and
    a wireless transceiver which is configured to receive the power from the battery and transmit the digital data stored in the memory to a network connector in response to a signal sent from the network connector.

15. The intraoral sensing apparatus according to claim 14, wherein
    the sensor is configured as at least one selected from a group consisting of a temperature sensor, an acceleration sensor, a gyro sensor, a pressure sensor, a strain sensor, a pulse wave sensor that measures pulse waves using light, a pulse oximeter that measures a blood oxygen concentration using light, a heart rate sensor that measures a heart rate using light, and a laser sensor that measures a blood flow using laser light.

16. The intraoral sensing apparatus according to claim 1, wherein
    the intraoral instrument is an orthodontic device, a denture, or a dental implant.

17. The intraoral sensing apparatus according to claim 1, wherein
the intraoral instrument is formed of a material capable of transmitting light with any wavelength in the range of 400 nm to 1000 nm.

18. The intraoral sensing apparatus according to claim 1, wherein
the second dental resin material is softer than the first dental resin material.

* * * * *